United States Patent [19]

Smith et al.

[11] 4,211,948
[45] Jul. 8, 1980

[54] FRONT SURFACE MATCHED PIEZOELECTRIC ULTRASONIC TRANSDUCER ARRAY WITH WIDE FIELD OF VIEW

[75] Inventors: Lowell S. Smith, Schenectady; Axel F. Brisken, Ballston Lake, both of N.Y.

[73] Assignee: General Electric Company, Schenectady, N.Y.

[21] Appl. No.: 958,654

[22] Filed: Nov. 8, 1978

[51] Int. Cl.² .............................................. H01L 41/10
[52] U.S. Cl. ..................................... 310/322; 310/326; 310/334; 128/660; 73/644; 367/152
[58] Field of Search ............... 310/322, 326, 323, 334, 310/335, 336, 337; 340/8 R, 8 MM, 8 L; 73/570, 587, 603, 605, 625, 627, 628, 629, 632, 642, 644; 128/660, 663

[56] References Cited
U.S. PATENT DOCUMENTS

| | | | |
|---|---|---|---|
| 2,527,217 | 10/1950 | Hayes | 340/8 MM |
| 2,844,809 | 7/1958 | Batchelder | 310/337 X |
| 3,277,451 | 10/1966 | Parssinen | 340/8 MM |
| 3,657,181 | 4/1972 | Riedesel et al. | 340/8 MM X |
| 3,964,014 | 6/1976 | Tehon | 340/10 X |
| 4,016,530 | 4/1977 | Goll | 340/8 MM X |
| 4,101,795 | 7/1978 | Fukumoto et al. | 310/336 |
| 4,122,725 | 10/1978 | Thompson | 310/336 X |

*Primary Examiner*—Mark O. Budd
*Attorney, Agent, or Firm*—Donald R. Campbell; James C. Davis; Marvin Snyder

[57] ABSTRACT

An ultrasonic transducer array with high sensitivity, for use in water tanks and with human subjects in steered beam imagers to make wide angle sector scans, has narrow transducer elements and one or more quarter-wavelength impedance matching layers on the front surface of each element. The matching layers as well as the piezoelectric ceramic are completely cut thorugh and guide acoustic energy incident at any angle to the ceramic. A continuous covering or wear plate is attached to the matching layers and a continuous damping material can cover the backs of the elements.

7 Claims, 7 Drawing Figures

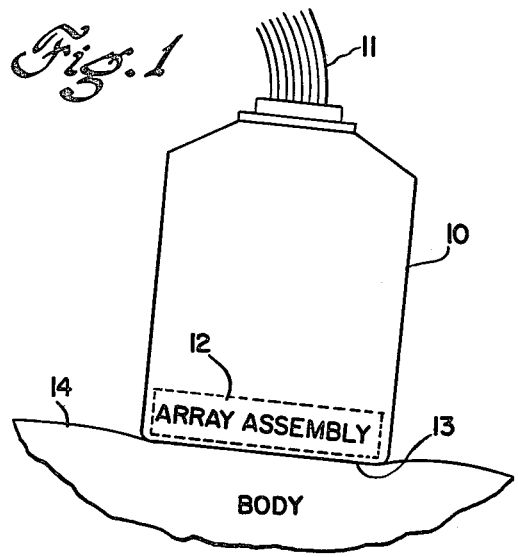
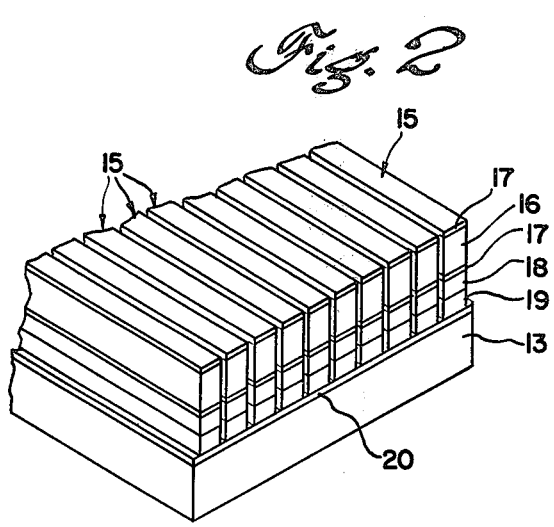
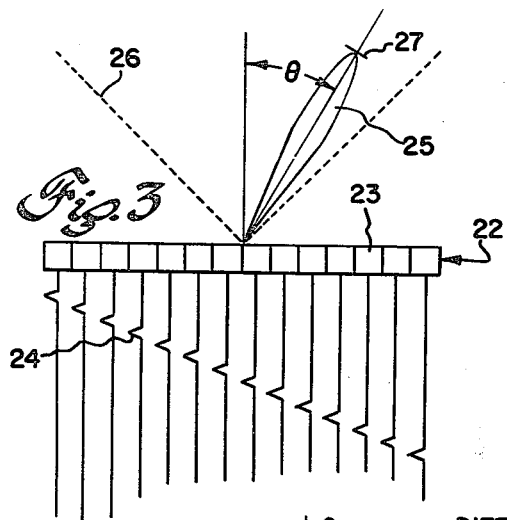
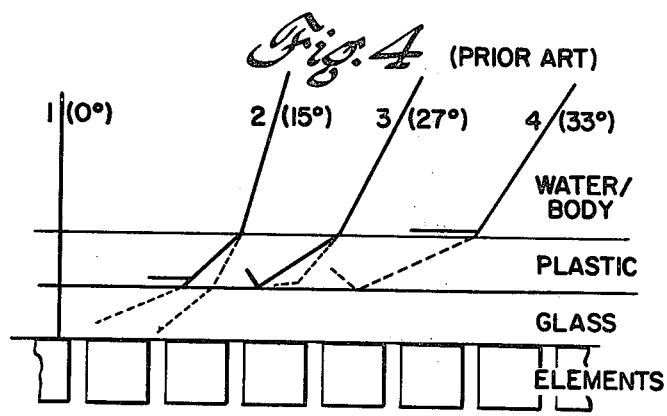
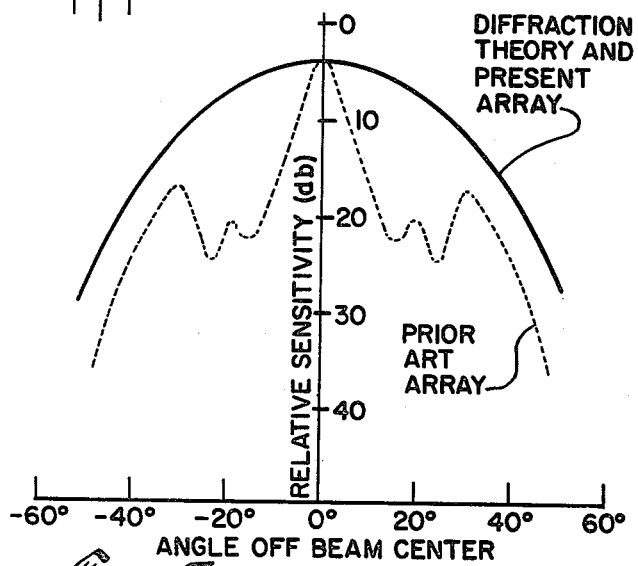
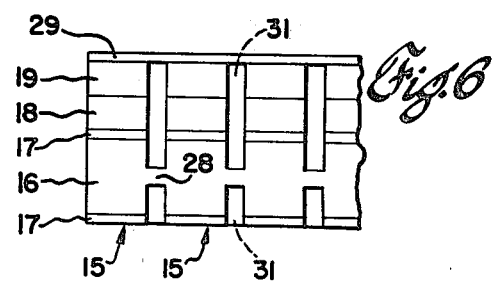
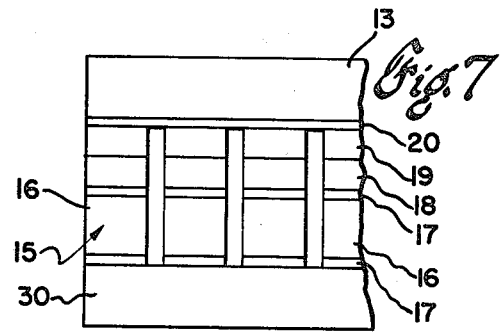

FRONT SURFACE MATCHED PIEZOELECTRIC ULTRASONIC TRANSDUCER ARRAY WITH WIDE FIELD OF VIEW

RELATED APPLICATION

This application is related to Ser. No. 958,655, "Wear Plate for Medical Ultrasonic Transducer Arrays", filed concurrently by the present inventors and assigned to the same assignee.

BACKGROUND OF THE INVENTION

This invention relates to ultrasonic transducer arrays and a method for their fabrication, and especially to arrays with impedance matching layers on the front surface for use in medical ultrasound examinations and water tank applications.

The general technique for high sensitivity ultrasonic transducers has been described. The crucial feature is that with two quarter wave matching transformers there is greatly improved energy transfer from the high impedance sources, such as piezoelectric ceramic, to water or to a human body. On known arrays both matching layers are continuous.

Currently manufactured transducer arrays commonly have a solid wear plate covering the surface of the array which is made of an epoxy-like material. This plastic acts as an inefficient matching layer and also refracts acoustic energy away from the ceramic except for incidence angles small (typically less than ±20°) compared to those required by a wide angle sector scanner.

The transducer array for a phased array sector scan imaging system must have a broad field of view, high sensitivity, and short impulse duration, and the prior art does not satisfy all these requirements.

SUMMARY OF THE INVENTION

A front surface matched transducer array for use with human subjects and in water tanks for performing wide angle sector scans is comprised of substantially acoustically isolated and physically separated transducer element and impedance matching layer unit assemblies, each including a narrow element and one or more quarter-wavelength matching layers for transforming the high acoustic impedance of the element (approximately $20-35 \times 10^5$ g/cm$^2$-sec) to the low acoustic impedance of the human body and water (approximately $1.5 \times 10^5$ g/cm$^2$-sec). Both the elements and the matching quarter wave transformers have a width on the order of one wavelength or less at the ultrasound emission frequency. An incoming acoustic wave at any incident angle appears as a local variation in hydrostatic pressure and a subsequent acoustic wave propagates down the impedance matching "wave guide" into the element. The array has both a high sensitivity and a wide field of view.

The preferred embodiment for making 90° sector scan transducer arrays has a piezoelectric element, a first matching layer of borosilicate glass, and a second matching layer of acrylic resin plastic. To fabricate the arrays the matching layers as well as the ceramic are completely cut through; a modification is that small bridges of material may be left between adjacent array units.

BRIEF DESCRIPTION OF THE DRAWINGS

FIG. 1 is a side view of the ultrasonic probe showing a block diagram of the array assembly covered on the front by a body contacting wear plate;

FIG. 2 is a fragmentary perspective view to an enlarged scale of the front surface matched transducer array and wear plate;

FIG. 3 is a sketch of a linear array for making a wide angle sector scan;

FIG. 4 is a schematic diagram of a prior art arrangement of continuous impedance matching layers bonded to isolated piezoelectric elements and the paths of acoustic rays incident at four different angles;

FIG. 5 is a curve of relative sensitivity vs. angle off normal for the front matched array contrasted with the prior art array in FIG. 4; and FIGS. 6 and 7 are partial side views of modifications of FIG. 2 in which the elements and matching layers are not completely cut through and small bridges are left between elements, and in which a continuous layer of damping material is attached to the backs of the elements.

DESCRIPTION OF THE PREFERRED EMBODIMENTS

In FIG. 1, ultrasonic probe 10 is held in the hand by a physician making a medical diagnostic examination and is connected by cables 11 to the remainder of a real time steered beam imaging system. Transducer array assembly 12 at the front of the probe is covered by a wear plate 13 which is directly in contact with the skin over the area of a patient's body 14 under investigation, and the probe is freely moved about while observing the image on a cathode ray tube to locate the body structure of interest and realize the best image. It is standard practice during ultrasound examinations to place a coating of a gel between the wear plate and patient in order to assure good acoustic coupling by excluding air pockets. Steered beam imagers are also known as phased array sector scanners, and the present front surface matched array makes possible wide angle sector scans with a total scan angle exceeding about 60° using a transducer array with narrow elements having a width on the order of one wavelength or less at the ultrasound emission frequency. Front surface matched array 12 has both high sensitivity and a large field of view. The performance is achieved by the use of impedance matching layers on the front surface of the array and saw cuts from the front surface all the way through the matching layers and through the piezoelectric ceramic. The array is also intended for use in water tanks such as for the nondestructive testing of metal and ceramic parts.

The preferred embodiment of front surface matched array 12 has two quarter-wavelength impedance matching layers, and its assembly to wear plate 13 is illustrated in FIG. 2. The matched array is comprised of a large number of individual piezoelectric ceramic element and impedance matching layer units or unit assemblies 15 that are substantially isolated from one another and acoustically uncoupled. Every array unit includes a narrow piezoelectric ceramic transducer element 16 which has a metallic coating 17 on opposite faces to serve as electrodes and a thickness between metallic coatings of one-half wavelength at the emission frequency since the element is a half wave resonator. Impedance matching layers 18 and 19 both have a uniform thickness of one-quarter wavelength at the emission frequency and serve as acoustic quarter wave matching transformers. Layer 18 is made of Pyrex ® borosilicate glass, or other glass with the required acoustic impedance, and layer 19 is made of Plexiglass ® acrylic resin plastic, or other plastic with the proper value of acoustic impedance. Quarter wave transformers 18 and 19 greatly improve energy transfer between the high impedance piezoelectric ceramic and the low impedance of the human body or water (the human body is largely water). The acoustic impedance of PZT (lead zirconate titanate) piezoelectric ceramic is about $30 \times 10^5$ g/cm²-sec and that of the body and water is about $1.5 \times 10^5$ g/cm²-sec, and for this transducer material the Pyrex layer has a value of acoustic impedance of $13.1 \times 10^5$ g/cm²-sec and the value for the Plexiglas layer is $3.2 \times 10^5$ g/cm²-sec.

Wear plate 13 is made of a material in which the longitudinal sound velocity is equal to or less than that in the human body and in which the acoustic impedance for longitudinal sound waves is approximately equal to that of the body. Refraction, if it occurs, enhances the field of view and the wear plate further does not change the pulse shape of the transducer waveform. Another property is that its exhibits sufficient mechanical strength to prevent damage to the array structure at nominal body contact. Such a wear plate is disclosed and claimed in application Serial No. 958,655, and two appropriate materials are filled silicone rubber (General Electric Company RTV-28) and polyurethane epoxy (Emerson & Cumings, Inc. STY CAST ® CPC-19 Room Temperature Curing Polyurethane). The wear plate can be many wavelengths thick and has a low acoustic absorption, and the foregoing materials can be conveniently cast onto the front surface of the transducer array as viscous liquids which cure in several hours to solids. It is useful to place a thin layer of Mylar ® tape 20, which is a film of polyethylene terephthalate resin, between the array and wear plate material so that liquid does not infiltrate the slots between the elements. The tape surface is primed so that the wear plate adheres easily to it.

The front surface matched transducer array is fabricated by bonding together a three-ply composite composed of the required layers and then making parallel cuts completely through the bonded composite at distances of one wavelength or less at the emission frequency. The slab of piezoelectric ceramic is either purchased at the correct thickness or is lapped from a slightly thicker slab. Thin metallic coatings are applied to opposite surfaces of this slab to provide the electrodes 17. Preferably, the ceramic is copper plated with an electroless process and is then gold electroplated. The glass is best reduced to the proper thickness of one-quarter wavelength by a double face lap or surface grinder; the Plexiglas is best reduced to a uniform quarter wavelength thickness by a double face lap or on a milling machine using a fly cutter. The ceramic and plastic layers are bonded to either side of the glass with Techform Laboratories, Inc. TC-2490 impregnating epoxy. This material has very low viscosity allowing for a uniform application without air bubbles and further has excellent adhesion exceeding that of the ceramic/gold interface. After lamination of the front surface matched structure, parallel cuts are made at a spacing of one wavelength using a semiconductor dicing saw, and the cuts pass completely through the bonded composite including ceramic, glass, and plastic layers. Wear plate 13 is then assembled onto the front surface of the array as previously described.

The present transducer array is characterized by elements and array unit assemblies that are substantially isolated and acoustically uncoupled, or which are free to vibrate independently. The element width at the front of every unit assembly 15 is limited to a dimension small compared to a wavelength. In this case, an incoming acoustic wave at any incident angle passes through wear plate 13 and appears as a local variation in hydrostatic pressure and a subsequent acoustic wave will propagate down the impedance matching "wave guide" comprised of plastic and glass layers 19 and 18 into piezoelectric ceramic 16. There is insufficient width for the wave phenomena of refraction to occur. The small element width at the front surface of plastic layer 19 will thus radiate and receive acoustic energy according to diffraction theory (to first order), as sketched in FIG. 5. To further understand the improvement over the prior art, the principles of sector scan imagers are reviewed with reference to FIG. 3 and a typical prior art array with continuous impedance matching quarter wavelength glass and plastic layers is explained with reference to FIG. 4.

Linear transducer array 22 in FIG. 3 is comprised of a large number of piezoelectric transducer elements 23 which are energized by excitation pulses 24 in a linear time sequence to form an ultrasound beam 25 and direct the beam in a preselected azimuth direction to transmit a pulse of ultrasound. In order to steer the beam electronically to an angle $\theta$ degrees from the normal to the array longitudinal axis at the sector origin point, a time delay increment is added successively to each signal as one moves down the array from one end to the other to exactly compensate for the propagation path time delay differences that exist under plane wave (Fraunhofer) conditions. First order corrections to the time delays will allow the system to also operate in the near field (Fresnel). By progressively changing the time delay between successive excitation pulses, the angle on one side of the normal is changed by increments, and to form an acoustic beam at the other side of the normal, the timing of excitation pulses 24 is reversed so that the right-hand transducer is energized first and the left-hand transducer is energized last. The total sector scan angle indicated by dashed lines 26 is approximately 90°. Echoes returning from targets 27 such as body structures in the direction of the transmitted beam arrive at the transducer elements at different times necessitating relative delaying of the received echo signals by different amounts so that all the signals from a given point target are summed simultaneously by all elements of the array. The time delays of the individual echo signals are the same as during transmission to compensate for acoustic path propagation delay differences, and these are referred to as steering delays. Every receiving channel may also electronically and dynamically focus a received echo to compensate for the propagation path time delay differences from the focal point to the varying individual array element positions. The contributions from all receive elements are coherently summed and the focused echo signals are fed to a cathode ray tube or other display device where the sector-shaped image is built up scan line by scan line as echo information is received.

High sensitivity is achieved by the prior art array in FIG. 4, but the quarter wavelength impedance matching layers of glass and plastic are continuous and only the array elements themselves are isolated by cutting into or completely through the ceramic, with the result that acoustic energy incident at angles greater than approximately 20° is refracted away from the ceramic. Four traces are depicted for different angles of incidence; the solid line is for the longitudinal wave and the dashed line for the shear wave. At 0° incidence there is no refraction (trace 1). At 15.4°, the longitudinal wave in water is refracted as a longitudinal wave in the glass (trace 2) parallel to the lamination surface. At 27.2°, the same occurs except that the refracted wave is now a parallel shear wave (trace 3). At 33.3°, the longitudinal wave in water is refracted as a parallel longitudinal wave in the plastic (trace 4). Beyond a 27.2° incidence angle, the acoustic energy can no longer reach the transducer element by a direct path. The dashed curve in FIG. 5 gives the observed signal level as a function of incidence angle in a transducer array of this architecture, and the observed pattern falls far short of that desired, specifically a diffraction limited pattern.

The solution to this limited field of view for a front surface matched array is the full isolation of elements and the complete through cutting of the front surface matching layers and the ceramic as depicted in FIG. 2. The array of physically separated elements is a diffraction grating, and the best achieveable pattern is a diffraction limited radiation pattern. The present matched array has a radiation pattern of this type as shown in solid line in FIG. 5. The waveform maintains its integrity over the entire field of view although the amplitude goes down at the edges. In the prior art array of FIG. 4, the front surface of the transducer element is the radiator, but in the present array of FIG. 2 the front surface of plastic impedance matching layer 19 is the radiator. This small array unit assembly width radiates and receives acoustic energy according to diffraction theory to first order.

An alternate to cutting completely through the entire laminated structure is to cut from both sides and to leave a thin solid bridge between adjacent unit assemblies 15, which can be in the glass, plastic, or piezoelectric ceramic layers. A preferred configuration illustrated in FIG. 6 is to leave a thin solid bridge 28 between adjacent elements 16. The transducer elements and the element and impedance matching layer assemblies 15 are then partially isolated and acoustically uncoupled. The front surfaces of impedance matching layers 19 in this figure can be covered only by a thin plastic membrane 29 to prevent liquid infiltrating between the elements during operational use or by a full wear plate as in FIG. 2. This embodiment of the front surface matched array is suitable for water bath operations. Alternatively, a light epoxy foam 31 may be infiltrated between the element and impedance matching layer unit assemblies 15.

FIG. 7 is a modification of the medical ultrasonic probe in FIG. 2, and further has a continuous layer of damping material 30 such as epoxy attached to the back surfaces of all the transducer elements 16. For high excitation levels the addition of the damping material results in a higher quality image. Layer 30 is relatively thick and should have a variable thickness rather than having a uniform width, and while there is a small additional signal loss, there is a great increase in the mechanical integrity of the array.

The acoustic impedance of PNO (lead metaniobate) piezoelectric ceramic is about $20 \times 10^5$ g/cm$^2$-sec, and quarter wave transformers 18 and 19 are made of different materials. Impedances are determined by the equations $Z_1 = \sqrt[3]{Z_b^2 Z_c}$ and $Z_2 = \sqrt[3]{Z_b Z_c^2}$, where $Z_b$ and $Z_c$ are the characteristic impedances of the body and ceramic, respectively. The invention can be practiced with one or three or more impedance matching layers, but materials with the requisite acoustic impedance values are not so readily available. With one matching layer the optimum impedance is given by the expression $Z = \sqrt{Z_b Z_c}$, and for PZT ceramic the impedance is $6.7 \times 10^5$ g/cm$^2$-sec. With PNO ceramic the impedance of a single matching layer is $5.5 \times 10^5$ g/cm$^2$-sec, and a two layer system requires impedances of $8.4 \times 10^5$ g/cm$^2$-sec and $3.6 \times 10^5$ g/cm$^2$-sec. The ideal impedance for a two layer system with PZT are $11.1 \times 10^5$ g/cm$^2$-sec and $4.1 \times 10^5$ g/cm$^2$-sec. The impedances of glass and plastic mentioned above represent a close approximation with readily available materials.

In conclusion, these transducer arrays for a wide angle sector scan imaging system are characterized by the combination of a large field of view with high sensitivity and short impulse duration. Medical ultrasound systems have applications in cardiology and laminography.

While the invention has been particularly shown and described with reference to several preferred embodiments thereof, it will be understood by those skilled in the art that various changes in form and details may be made therein without departing from the spirit and scope of the invention.

The invention claimed is:

1. An ultrasonic probe for use in steered beam imaging systems comprising:
    a front surface matched linear transducer array for transmitting pulses of ultrasound with a preselected emission frequency along many radial scan lines to perform a wide angle sector scan with a total angle exceeding 60° and for detecting echoes reflected by an object being examined;
    said matched array being comprised of substantially isolated and acoustically uncoupled transducer element and impedance matching layer unit assemblies each including a narrow element to which is secured at least one quarter-wavelength matching layer for transforming the high acoustic impedance of the element to a low acoustic impedance approximately equal to that of the human body, the element and matching layer in every unit assembly both having a width in the direction of the longitudinal axis of the array on the order of one wavelength or less at the ultrasound emission frequency whereby acoustic energy incident at any angle is guided through the matching layer to the element without being refracted; and
    a continuous covering attached to the matching layer of all of said unit assemblies.

2. The ultrasonic probe of claim 1 wherein the individual element and matching layer unit assemblies are completely separated from one another.

3. The ultrasonic probe of claim 1 wherein the individual element and matching layer unit assemblies are connected to adjacent unit assemblies by a narrow bridge.

4. The ultrasonic probe of claim 1 further including a continuous layer of damping material attached to the back surface of all said elements.

5. An ultrasonic probe for use in steered beam imaging systems comprising:

a front surface matched linear transducer array for transmitting pulses of ultrasound with a preselected emission frequency along many radial scan lines to perform an approximately 90° sector scan and for detecting echoes reflected by the object being examined;

said matched array being comprised of plural transducer element and impedance matching layer unit assemblies which are physically separated from one another and free for independent vibration, each unit assembly including a narrow element with a width on the order of one wavelength or less at the ultrasound emission frequency to which are secured first and second quarter-wavelength matching layers of the same width for transforming the high acoustic impedance of the element to a low acoustic impedance approximately equal to that of the human body, whereby acoustic energy incident at any angle is guided through the matching layers to the element without being refracted; and a continuous wear plate attached to the second matching layer of all of said unit assemblies.

6. The ultrasonic probe of claim 5 further including a continuous layer of damping material attached to the back surface of all said transducer elements.

7. The ultrasonic probe of claim 6 wherein said transducer element is a piezoelectric ceramic and said first and second impedance matching layers are a borosilicate glass and an acrylic resin plastic.

* * * * *